United States Patent [19]
Nemet-Mavrodin

[11] Patent Number: 4,704,492
[45] Date of Patent: Nov. 3, 1987

[54] SELECTIVE HYDROGENATION OF ACETYLENIC IMPURITIES IN CRUDE BUTADIENE

[75] Inventor: Margaret Nemet-Mavrodin, Robbinsville, N.J.

[73] Assignee: Mobil Oil Corporation, New York, N.Y.

[21] Appl. No.: 946,227

[22] Filed: Dec. 24, 1986

[51] Int. Cl.[4] .................. C07C 5/03
[52] U.S. Cl. .................. 585/259; 585/258; 585/260
[58] Field of Search .................. 585/258, 259, 260

[56] References Cited

U.S. PATENT DOCUMENTS

| | | | |
|---|---|---|---|
| 4,367,353 | 1/1983 | Inglis | 585/259 |
| 4,469,907 | 9/1984 | Araki | 585/259 |
| 4,493,906 | 1/1985 | Couvillion | 585/260 |
| 4,587,369 | 5/1986 | Casyns et al. | 585/259 |

*Primary Examiner*—Curtis R. Davis
*Attorney, Agent, or Firm*—A. J. McKillop; V. D. Harrison, Jr.; M. G. Gilman

[57] ABSTRACT

In a process wherein the vinyl acetylenes present as an impurity in a stream of butadienes are removed by hydrogenating the stream over a catalyst the loss of butadiene is lessened and catalyst aging is diminished by injecting the hydrogen in reduced quantities into a series of smaller catalyst beds connected in series.

6 Claims, 2 Drawing Figures $H_2$
3
4D
4C
4B
4A
2D
2C
2B
2A
5
6
7
8
9
1
10
IMPURE BUTADIENE

SELECTIVE HYDROGENATION OF ACETYLENIC IMPURITIES IN CRUDE BUTADIENE

NATURE OF THE INVENTION

This invention relates to processes wherein raw streams of diolefins and olefinic hydrocarbons containing high levels of acetylenic impurities are hydrogenated to reduce the concentration of the acetylenic materials.

BACKGROUND OF THE INVENTION

The refining of petroleum hydrocarbons often results in a refinery stream which will comprise mainly a gas or liquid stream of high butadiene content containing also thiolefinic and acetylenic hydrocarbons. The upgrading of the butadiene content in this fraction is possible only after removal of butyne and vinyl acetylene. One technique of upgrading the stream by removing the acetylenic compounds present is by selective hydrogenation. Techniques for selective hydrogenation of the acetylenics content are discussed in U.S. Pat. Nos. 4,587,369 and 4,493,906, both of which are incorporated herein by reference. The processes described in those patents rely primarily on a catalyst which in one instance will be a palladium on alumina catalyst, and in the other instance, a copper metal dispersed on gamma alumina. In the processes described therein it is, of course, desirable to minimize the loss of butadiene and butylene resulting from hydrogenation and oligomerization, and to reduce the rate of catalyst aging.

Accordingly a primary object of this invention is to provide a process wherein impure streams of butadiene can be purified by the hydrogenation of acetylenic compounds present therein using a catalyst agent. Still another object of this invention is to diminish the rate of catalyst aging. Another object of this invention is to provide a method for minimizing butadiene loss.

SUMMARY OF THE INVENTION

Briefly stated, this invention comprises a method for selectively hydrogenating the acetylene compounds present in a given stream of butadiene and butene wherein the liquefied gas being treated is flowed through a series of reactor beds and simultaneously hydrogen is introduced into each of the reactor beds and contacted with the liquid hydrocarbon flowing therethrough. In each bed the ratio of moles of hydrogen introduced to the number of moles of acetylenes originally put into the system is diminished. Results using this technique have shown that this process results in a better conversion of the vinyl acetylenes and a corresponding reduced loss of butadiene due to overhydrogenation and oligomerization, and slower catalyst aging.

DESCRIPTION OF THE INVENTION

Figure 1:
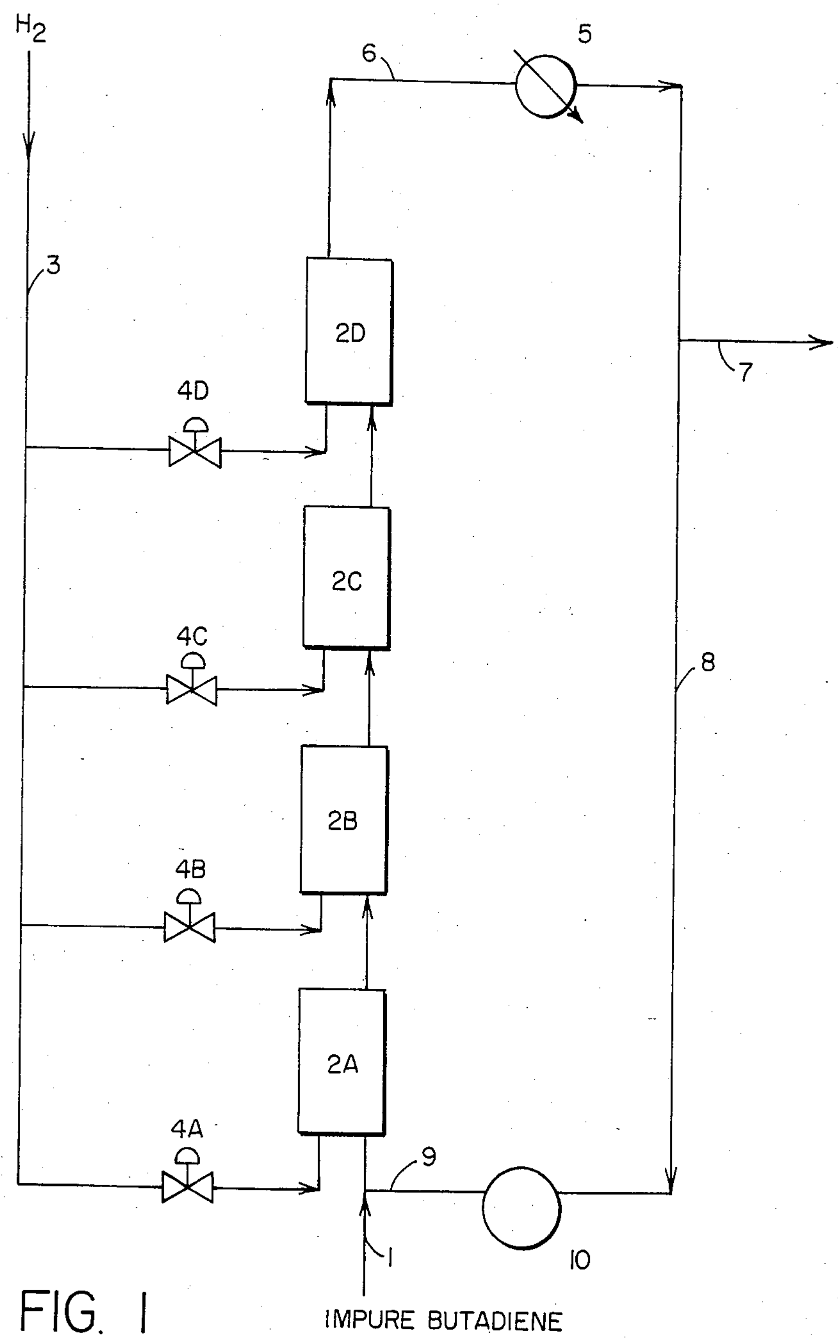
FIG. 1 presents a schematic drawing of one embodiment of this invention wherein impure liquid butadiene is flowed sequentially through a series of catalyst beds into each of which beds hydrogen is injected, the rate of hydrogen injection being less in each bed in relation to the initial amount of feedstock used.

Referring now to FIG. 1, the liquid butadiene stream to be hydrogenated is introduced through line 1. Hydrogen is made available to each of a plurality of catalyst beds 2A, 2B, 2C and 2D through line 3 and flow control valves 4A, 4B, 4C and 4D. The catalyst beds comprise a series of reactor beds, each one filled with a suitable hydrogenating catalyst such as the copper-gamma alumina catalyst known in the prior art or palladium on alumina. Hydrogen is introduced into each of the catalyst beds shown in FIG. 1 near the bottom of each reactor. Beginning with bed 2A and extending through bed 2B the amount of hydrogen injected into each of the catalyst beds will diminish. For example, if the ratio of the flow of moles of hydrogen through valve 4A to the flow of moles of acetylenes originally in the feedstock in line 1 into reactor 2A is 0.7, the number of moles of gas injected through valve 4B will be from 0.4 to 0.8 moles per mole of acetylenes per hour and that through 4D 0.1 to 0.2 moles per mole of acetylene. An overall ratio of total moles of hydrogen injected into the system per mole of acetylenes is between 1 and 2.

After being cooled in the exchanger 5 the effluent mixture (line 6) is further processed and purified (line 7). If desired, a portion of the effluent product is recycled to the feedstream 1 through lines 8 and 9. Ordinarily the pressure in the reactor chambers will be between 100 and 400 psig and the temperature in these reactors will vary from 40° to 70° C.

EXAMPLE 1

In this first test a feedstream containing 1.7 wt.% vinyl and 0.2 wt.% ethyl acetylene in the feedstock was passed through a series of four beds at an overall weight hourly space velocity in terms of the acetylenes of 0.011. The operating temperature was between 55° and 56° C. and the operating pressure was 175 psig. In each of the four beds hydrogen was introduced in a ratio starting from between 0.71 and 0.77 moles per mole of acetylenes in the first bed and diminishing to between 0.13 and 0.14 moles per mole of acetylenes in the fourth bed. The overall hydrogen-to-acetylenes molar ratio was 1.66. The catalyst used was copper on alumina. In a series of material balances run on the apparatus the following results were obtained:

| Mat. Balance | Product Vinyl Acetylene, Wt. % | Product Ethyl Acetylene, Wt. % | 1,3-Butadiene Loss % |
|---|---|---|---|
| 1 | 0.061 | 0.157 | 1.33 |
| 2 | 0.055 | 0.153 | 1.36 |
| 3 | 0.052 | 0.151 | 1.35 |
| 4 | 0.052 | 0.151 | 1.13 |
| 5 | 0.048 | 0.148 | 0.99 |
| 6 | 0.033 | 0.128 | 1.41 |
| 7 | 0.032 | 0.126 | 1.28 |
| 8 | 0.021 | 0.133 | 1.25 |
| 9 | 0.042 | 0.143 | 1.24 |
| 10 | 0.050 | 0.149 | 1.20 |
| 11 | 0.061 | 0.158 | 1.24 |

EXAMPLE 2

In a test duplicating or nearly duplicating the prior art, a liquid feedstock of a composition essentially the same as that in the preceding example (1.75 wt.% vinylacetylene, and 0.23 wt.% ethylacetylene) was run. The weight hourly space velocity in terms of acetylenes was again 0.011. The molar ratio of the total hydrogen to acetylenes injected was 1.63. Operating temperature was again between 55° and 56° C. and operating pressure was 175 psig. Results obtained were as follows:

| Mat. Balance | Product Vinyl Acetylene, Wt. % | Product Ethyl Acetylene, Wt. % | 1,3 Butadiene Loss % |
|---|---|---|---|
| 1 | 0.019 | 0.105 | 2.26 |
| 2 | 0 | 0.107 | 1.84 |
| 3 | 0.021 | 0.115 | 2.01 |
| 4 | 0.025 | 0.115 | 1.84 |
| 5 | 0.033 | 0.121 | 1.75 |
| 6 | 0.034 | 0.123 | 1.73 |

EXAMPLE 3

Figure 2:
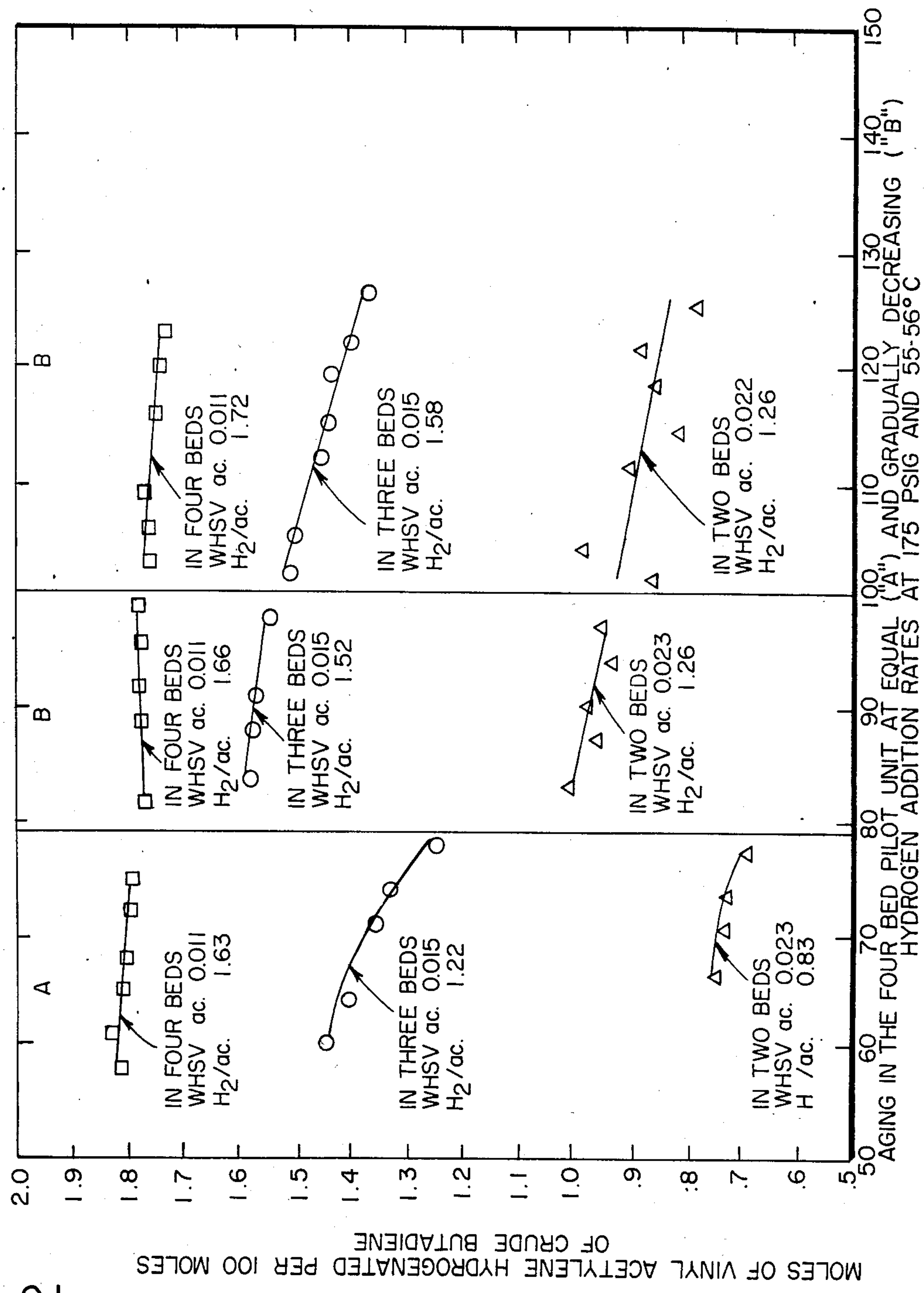
In FIG. 2 there are presented graphs showing the effect of using applicant's process and the improved results thereby obtained.

In a similar test a four-bed pilot unit was used in which aging at both operating modes was tested. The results obtained are presented in FIG. 2.

Comparison of the foregoing data will readily show that the results obtained using decreasing amounts of hydrogen in separate beds does result in less percentage loss of butadiene and also slower catalyst aging.

What is claimed is:

1. In a process for hydrogenating acetylenic compounds present in a liquid hydrocarbon stream containing butadiene compounds wherein said liquid stream is passed in contact with a catalyst bed and with hydrogen gas, the improvement comprising dividing the catalyst bed into a series of reactor beds and injecting hydrogen gas into each reactor bed, the amount of hydrogen gas injected into each bed being substantially less than that of the preceding bed as said stream moves downstream.

2. The process of claim 1 wherein the catalyst is copper on alumina.

3. The process of claim 1 wherein the catalyst is palladium on alumina.

4. The process of claim 1 wherein the ratio of overall hydrogen injected to acetylenes present in the raw feedstream is between about 1 and about 2 moles per mole.

5. The process of claim 1 wherein the ratio of moles of hydrogen gas injected into the first of the series of beds to the moles of acetylenic compounds in the feedstream is between about 0.4:1 to about 0.8:1.

6. The process of claim 1 wherein the ratio of moles of hydrogen gas injected into the last of the series of reactor beds is between about 0.1:1 to about 0.2:1.

* * * * *